(12) United States Patent
Hauk et al.

(10) Patent No.: US 8,293,793 B2
(45) Date of Patent: Oct. 23, 2012

(54) PRODUCTION OF ACID PROPIONATES

(75) Inventors: Alexander Hauk, Ludwigshafen (DE); Stefan Gropp, Ludwigshafen (DE); Gerd Diebold, Reutlingen (DE); Florian Weigel, Deidesheim (DE); Gerhard Laux, Frankenthal (DE)

(73) Assignee: BASF SE, Ludwigshafen (DE)

( * ) Notice: Subject to any disclaimer, the term of this patent is extended or adjusted under 35 U.S.C. 154(b) by 769 days.

(21) Appl. No.: 12/159,513

(22) PCT Filed: Dec. 29, 2006

(86) PCT No.: PCT/EP2006/070269
§ 371 (c)(1),
(2), (4) Date: Jun. 27, 2008

(87) PCT Pub. No.: WO2007/077200
PCT Pub. Date: Jul. 12, 2007

(65) Prior Publication Data
US 2008/0317934 A1    Dec. 25, 2008

(30) Foreign Application Priority Data
Dec. 30, 2005   (DE) .......................... 10 2005 063 109

(51) Int. Cl.
*A61K 31/19*   (2006.01)
*C07C 53/00*   (2006.01)
(52) U.S. Cl. ........................................ 514/578; 562/606
(58) Field of Classification Search .................. None
See application file for complete search history.

(56) References Cited

U.S. PATENT DOCUMENTS

| | | | |
|---|---|---|---|
| 3,008,986 A * | 11/1961 | Hyson ........................... | 562/606 |
| 4,112,122 A | 9/1978 | Long | |
| 4,179,522 A | 12/1979 | Huitson | |
| 4,401,624 A * | 8/1983 | Atwater ........................... | 422/12 |
| RE32,416 E * | 5/1987 | Long ............................... | 426/19 |

FOREIGN PATENT DOCUMENTS

| | | |
|---|---|---|
| DE | 2432473 A1 | 1/1976 |
| DE | 2653449 A1 | 6/1977 |
| DE | 2722919 A1 | 12/1977 |
| EP | 0032807 A1 | 7/1981 |
| EP | 0112080 A1 | 6/1984 |
| EP | 0123416 A1 | 10/1984 |
| GB | 1473447 | 5/1977 |

OTHER PUBLICATIONS

Levi, T. G., "Acid Salts of Fatty Acids", Gazzetta Chimica Italiana, 1932, vol. 62, pp. 709-716.
"Solubility in the Calcium Propionate-Propionic Acid-Water System at 50 and 60 Degree", Database CA, Accession No. 1984:598946.

* cited by examiner

*Primary Examiner* — Paul A Zucker
(74) *Attorney, Agent, or Firm* — Connolly Bove Lodge & Hutz LLP

(57) ABSTRACT

The present invention relates to propionic acid-comprising compositions in solid and essentially pure form comprising at least one compound according to formula (I)

$$(M^{n+})(H^+)_x(CH_3CH_2C(O)O^-)_{(n+x)} \qquad (I),$$

where $M^{n+}$ is an n-valent alkali metal cation or alkaline earth metal cation, n being equal to 1 or 2; and x is a number in the range from 0.25 to 5;

with the proviso that x is not in the range from 0.75 to 1.75 when $M^{n+}$ is potassium; a method for producing such propionic acid-comprising compositions; and also the use of such compositions as silage additive, preservative, acidifier, food supplement, feedstuff or feedstuff additive for animal feed.

5 Claims, No Drawings

PRODUCTION OF ACID PROPIONATES

RELATED APPLICATIONS

This application is a national stage application (under 35 U.S.C. §371) of PCT/EP2006/070269, filed Dec. 29, 2006, which claims benefit of German application 10 2005 063 109.6, filed Dec. 30, 2005.

The present invention relates to propionic acid-comprising alkali metal and alkaline earth metal salts in solid form, methods for their production, their use as silage additives, preservatives, acidifiers, food supplements, feedstuffs or feedstuff additive for animal feed.

Propionic-acid-comprising alkali metal and alkaline earth metal salts and media (usually liquid) comprising these have an antimycotic activity and can serve, for example, for preservation and acidification of plant and animal material, for instance grasses, agricultural products or meat, in addition as additive for human or animal nutrition. In particular, they are suitable as silage additives or silage aids in the production of silage, since the reduction in pH caused by them counteracts an emergence of putrefactive bacteria. Propionic acid present in such salts can accelerate lactic acid fermentation and prevent secondary fermentation.

With a few exceptions, these salts, also termed acid propionates, have previously only been described and used or proposed for use in dissolved form. This is due in particular to the fact that solid forms of these compounds, such as acid metal salts of low-molecular-weight carboxylic acids in general, are considered very unstable, which makes their production sometimes relatively complex (see e.g. EP 0 032 807 A1, p. 1, lines 3-14).

Adequate stability of these compounds, however, is of particular importance with regard to handling, storability and production. In particular, relatively great or uncontrolled release of the propionic acid present in the compounds, owing to its corrosive action, and because of its unpleasant odor, is undesirable.

DE 26 53 449 A1 and DE 27 22 919 A1 describe both, inter alia acid alkali metal dipropionates, and also acid alkaline earth metal tetrapropionates in dissolved form. In U.S. Pat. No. 4,401,624, buffered solutions which comprise, e.g., sodium dipropionate, are described having reduced corrosivity compared with free propionic acid.

EP 0 112 080 A1 describes the use of solid acid potassium propionate (potassium dipropionate) as preservative for animal feeds, but without specifying its production.

According to DE 24 32 473 A1, inter alia solid acid potassium propionate (potassium dipropionate) is said to be able to be produced by the fluidized-bed method described there.

The production of solid acid potassium propionate (potassium dipropionate) from aqueous or alcoholic solution of propionic acid and neutral potassium propionate by evaporation, filtration and washing with ethanol is disclosed by Levi, T. G., Gazzetta Chimica Italiana 1932, 62, 709-716. In this publication it is stated that further acid potassium propionates, such as for example acid potassium tripropionate, would not exist, or are not accessible by means of the process described there.

EP 0 123 416 A1 and EP 0 032 807 A1 also describe acid potassium propionate (potassium dipropionate) in solid form which was obtained by crystallization from an aqueous solution of propionic acid and neutral potassium propionate. In EP 0 032 807 A1, however, the potassium dipropionate is only a byproduct, since the method described there is primarily directed toward the production of solid dipotassium pentapropionate. While the method according to EP 0 123 416 A1 has to start from an equimolar solution of the abovementioned starting materials, in the method according to EP 0 032 807 A1, the molar ratio of these starting materials can vary. However, no explicit statements may be taken in this respect from EP 0 032 807 A1; in the examples, equimolar mixtures or a one and a half times excess of propionic acid are used. In the latter case, the resultant solid, however, is a mixture of potassium dipropionate and dipotassium pentapropionate.

U.S. Pat. No. 3,008,986 describes the production of solid acid sodium propionate which, as unwanted byproduct, comprises traces of sodium dipropionate in the range of a few hundred ppm.

In the field of animal nutrition, acid propionates offer, in particular, the advantage that wanted cations can be combined with a favorable nutritional value via these compounds. Especially sodium-comprising acid propionates offer the advantage that the trace element sodium need not be added separately as otherwise is customary in the form of NaCl, but is already present as a sodium source. Via a defined propionic acid content in sodium-comprising acid propionates, the content of sodium ions could in addition be controlled or restricted. A small or restricted content of cations, e.g. also of potassium ions, is desirable to the extent that the latter, in particular in the case of monogastric animals, and especially in the case of poultry, lead to an increased liquid intake (increased drinking) and thus to dilution of the feces of the animals, and consequently can exhibit a diuretic action.

It was therefore an object of the present invention to provide compounds as stable as possible in solid, in particular crystalline and/or dry form, which essentially comprise propionic acid, and alkali metal or alkaline earth metal propionates, and also methods for their production. These production methods should enable in particular controlled setting of the content and especially setting of a high content of propionic acid in the target compounds. In addition, the production methods should be able to be employed efficiently in the context of industrial production. For this reason, the inventive compounds should also be distinguished, in particular, by simple handling and especially by a comparatively low vapor pressure.

This object has surprisingly been achieved by obtaining the target compounds from a defined homogeneous mixture of propionic acid and the respective neutral alkali metal propionate or alkaline earth metal propionate, the mixture either being virtually anhydrous or at least having only a very low water content.

The present invention therefore relates to a method (A) for producing a propionic-acid-comprising composition in solid and essentially pure form, comprising at least one compound according to formula (I)

$$(M^{n+})(H^+)_x(CH_3CH_2C(O)O^-)_{(n+x)} \qquad (I),$$

where
$M^{n+}$ is an n-valent alkali metal cation or alkaline earth metal cation, e.g. lithium, sodium, potassium, rubidium, cesium, beryllium, magnesium, calcium, strontium or barium; preferably sodium, potassium, magnesium or calcium; and particularly preferably sodium or calcium; n being equal to 1 or 2; and x is a number in the range from 0.25 to 5; preferably in the range from 0.3 to 3.5; and particularly preferably in the range from 0.3 to 2.5;

in which a homogeneous mixture is produced from the neutral alkali metal propionate or alkaline earth metal propionate and propionic acid in a molar ratio in the range from 1:0.25 to 1:5; preferably in the range from 1:0.3 to 1:3.5;

and particularly preferably in the range from 1:0.3 to 1:2.5, with heating, and the homogeneous mixture is solidified, and the water content of the homogeneous mixture, at least at the start of solidification, and in particular also during it, being less than 1% by weight, based on the total weight of the mixture.

Neutral alkali metal propionates and alkaline earth metal propionates means here and hereinafter those which have no content of protons. Preferably, use is made of the neutral propionates of the following metals: lithium, sodium, potassium, rubidium, cesium, beryllium, magnesium, calcium, strontium or barium; particularly preferably sodium, potassium, magnesium or calcium; and very particularly preferably sodium or calcium. Such neutral propionates and methods for their production are known to those skilled in the art; some of these compounds are also commercially available, e.g. sodium propionate (E281), potassium propionate (E283) and calcium propionate (E282).

A customary procedure for production of the neutral propionates to be used is, e.g., reacting the respective alkali metal or alkaline earth metal hydroxide, carbonate or hydrogen carbonate with propionic acid. In this variant, a procedure can be followed, e.g. such that the solid alkali metal hydroxide or alkaline earth metal hydroxide or a concentrated aqueous solution thereof, is dissolved, if appropriate with cooling and/or stirring, in preferably concentrated propionic acid. This mixture is then brought, if appropriate after neutralization of excess acid, to crystallization, e.g. by decreasing the water or acid content of the mixture, which proceeds by means of customary methods known to those skilled in the art, e.g. evaporation, extraction, distillation and the like. The crystallized neutral alkali metal propionate or alkaline earth metal propionate is then isolated by methods known to those skilled in the art for separating solid and liquid phases. Generally, use is made of a neutral propionate which comprises no more than 0.5% by weight, based on the total weight of the neutral propionate source used, of foreign constituents different from water. Preferably, use is made of a neutral propionate source which comprises less than 0.1% by weight, and in particular less than 0.05% by weight, in each case based on the total weight of the neutral propionate source used, of potassium ions.

Customarily, to produce the homogeneous mixture, use is made of a concentrated propionic acid having a propionic acid content of at least 95% by weight, and in particular at least 99% by weight, based on the total weight.

The homogeneous mixture of the starting materials can be produced by customary procedures known to those skilled in the art, e.g. by mixing, stirring or dissolving using elevated temperatures, e.g. above 30° C., or by a combined use of these methods. The sequence of use of the starting materials is of minor importance. Advantageously, the starting materials are combined in such a manner that a homogeneous liquid mixture of the starting materials in the desired molar ratio is obtained. If, after the combination, all components are not present completely in dissolved form, the temperature is elevated, preferably with stirring, until the desired melt or solution is obtained. During combination of the starting materials the reaction mixture is advantageously agitated, e.g. stirred. The agitation is continued until after completion of the combination at least until the melt or solution is obtained, in the latter case, customarily until the end or termination of crystallization.

According to the invention, the starting materials can be mixed in all apparatuses customarily used to produce a homogeneous liquid mixture, such as reactors, vessels, flasks etc., in particular in stirred tanks, especially those having internal heat-exchange surfaces. These are known to those skilled in the art. To avoid corrosion effects, e.g. in reactors or vessels made of steel, it is advantageous when the surfaces and walls coming into contact with propionic acid are coated with an acid-resistant protective layer, e.g. of Teflon®, or are lined with especially acid-resistant high-alloy steels.

According to the invention, the homogeneous mixture is produced with heating. This is taken to mean generally temperatures of at least 30° C., in particular at least 40° C., and especially at least 50° C., generally 250° C., and in particular 200° C., not being exceeded. The temperature required to achieve a homogeneous mixture will depend in the individual case on the type of metal cation used and also on the molar ratio of starting materials used. It is essential to the invention in the production method (A) that the heating generates a completely homogeneous mixture. This homogeneous mixture can be either a melt or a solution.

To carry out the method (A) according to the invention, generally a procedure is followed such that the starting materials are combined at room temperature. The combination can be simultaneously or sequentially, and independently of one another in each case in portions, e.g. in 1, 2, 3, 4 or more, in particular 2 to 20, and especially 3 to 10 portions, or continuously, i.e. at constant, decreasing or increasing rate. Subsequently, the reaction mixture is heated until the homogeneous mixture is obtained in the form of a melt or solution. Continuous addition of one or both starting materials can also proceed in such a manner that the starting material(s) brought to and held at room temperature is(are) added to the already heated reaction mixture. Customarily, the temperature of the mixture is set in such a manner, e.g. by matching the rate of addition and/or cooling or heating of the mixture and/or of the added starting materials, that in the mixture a temperature in the range from 30° C. to 200° C., and in particular in the range from 40° C. to 180° C., is maintained.

According to the invention the homogeneous mixture obtained in this manner is at least in part solidified. Depending on whether the homogeneous mixture is present in the form of a melt or solution, the solidification step can vary. Solidification means here that the mixture, in the case of a melt, is brought to setting (variant A1), or in the case of a solution, is brought to crystallization (variant A2). In the first case (A1), customarily the entire homogeneous mixture is brought to setting, if appropriate a small amount of residual moisture, in particular propionic acid, being present in the set product, e.g. less than 1% by weight, in particular less than 0.5% by weight, based on the total weight of the product (i.e. the resultant solid composition). Preferably, the set product comprises no fractions of residual moisture. In the latter case (A2), generally a solid phase is crystallized out of the liquid mixture, a part of the liquid phase being obtained as mother liquor.

The solidification is preferably caused by cooling the mixture, e.g. to a temperature of below 30° C., and in particular to room temperature, and/or by evaporation of volatile constituents of the mixture, in particular water or propionic acid, if appropriate under vacuum. The cooling or evaporation can, in the case of variant A2, proceed in the presence of seed crystals of the respective desired compound of the formula (I). Whether the reaction mixture, on cooling or evaporation, in addition to a solid phase comprising the compound of the formula (I), also forms a liquid phase (whether the solidification therefore proceeds according to variant A1 or A2), depends in the individual case on the type of metal cation used and also on the molar ratio of the starting materials used or on the stoichiometry of the resultant compound of the formula (I). This can be determined in a simple manner in the individual case by those skilled in the art by reproducing the production pathway described here.

If heating the homogeneous mixture leads to a melt (variant A1), this is generally brought to setting by cooling. In this case customarily a single solid phase is obtained which essentially comprises at least one, e.g. 1 or 2, compound(s) of the formula (I). An advantage of this variant of the method according to the invention is, in particular, that without using a drying step a dry product, e.g. having a residual moisture content of water and/or propionic acid of at most 1% by weight, based on the total weight of the product, is obtained. By means of a drying step, as described hereinafter, this residual moisture content can be reduced still further.

If heating the homogeneous mixture leads to a solution (variant A2), this is preferably brought to crystallization by cooling. In this case customarily a solid phase is obtained which essentially comprises one, e.g. 1 or 2, and in particular 1, compound(s) of the formula (I) and a liquid phase (mother liquor). After crystallization, the resultant solid product is separated off from the mother liquor. The solid phase can be separated off from the mother liquor by customary methods known to those skilled in the art for this, e.g. filtration or centrifugation, preferably via centrifugation, in particular using pusher or knife-discharge centrifuges. The product thus obtained generally still comprises small amounts of propionic acid, water and/or neutral propionate used, which can be reduced by a subsequent drying step, as described hereinafter.

If the setting (variant (A1)) is caused by cooling, this generally proceeds in the course of a few minutes. If the crystallization (variant (A2)) is caused by cooling, this preferably proceeds slowly, advantageously over a period of one or more hours, e.g. in the range from 1 to 48 h, in particular from 2 to 24 h, and especially from 4 to 12 h. In this case, the target compound crystallizes. Cooling can proceed, e.g. at a cooling rate in the range from about 1 to about 25 K/hr e.g. about 2 to 20 K/h. To achieve thorough crystallization of the target compound, it is advantageous to cool the reaction mixture in said period to a temperature of below 30° C., e.g. to room temperature or below. Generally in this case the temperature does not fall below 0° C., and in particular 5° C.

If, in the case of variant (A2), a solution is brought to crystallization by cooling it can be advantageous, after initiation of crystal formation, to redissolve the crystal seeds or small crystals first formed by repeated temperature elevation, e.g. by 5 to 10° C., or if necessary more, and to reinitiate the crystallization process subsequently by repeated, if appropriate slowed, cooling.

In addition, in the case of variant (A2) it can be advantageous to add to the solution preexisting e.g. produced in advance by the method according to the invention, crystals of the desired compound of the formula (I) to promote the crystallization process, i.e. for the purpose of what is termed "seeding". Such crystals can be added in dry or moist form, e.g. suspended in a liquid, preferably a propionic acid phase, or a combination of these forms. In this case the addition generally, but not necessarily, proceeds above a temperature which leads to spontaneous crystal formation, and in any case below a temperature at which the added seed crystals dissolve. Reaction mixture temperatures suitable in each case can be determined by those skilled in the art without problems in routine experiments. The crystallization process can then be continued as described above.

The product which, in particular in the case of variant (A2) is still moist can be dried by customary drying methods e.g. under vacuum and/or moderate heating. Dryers and drying methods which can be used for this are known to those skilled in the art and described in K. Kröll; Trockner und Trocknungsverfahren [Dryers and drying methods], 2nd edition, Springer Verlag, Berlin 1978. In particular, use can be made of, e.g., contact dryers, fluidized-bed dryers and radiant-heat dryers. It is also possible to use spray dryers, advantageously the steps of crystallization and drying proceeding in parallel. On drying, the relatively high volatility of the propionic acid present in the product and also if appropriate a limited temperature stability of the product, must be taken into account. During drying, customarily in the case of acid alkali metal propionates; product temperatures will not exceed 75° C., and in particular 50° C.; and in the case of acid alkaline earth metal propionates, product temperatures will not exceed 150° C.

The water content remaining in the product or in the resultant composition (residual water content) in variant (A1) after setting and a drying step, or in the case of (A2) after a drying step, is generally at most 1% by weight, preferably at most 0.5% by weight, and is customarily in the range from about 0.5 to 0.01% by weight, based on the total weight of the composition. In case (A1), the water content is particularly preferably at most 0.3% by weight, very particularly preferably at most 0.2% by weight, and frequently in the range from 0.25 to 0.01% by weight, based on the total weight of the composition. In this case the water content is determined in each case by oxidimetric titration according to Karl Fischer (e.g. described in Wiland, Wasserbestimmung durch Karl-Fischer-Titration [Water determination by Karl-Fischer titration], Darmstadt, GIT, 1985).

Here and hereinafter, the expression total weight of the composition is used synonymously with the expression total dry weight. The total dry weight is to be taken to mean the weight of the composition which is given by drying the product below its decomposition temperature, e.g. in the case of acid alkali metal propionates, by drying over a period of 1 h at a temperature of 40° C. and a pressure of 50 mbar, or in the case of acid alkaline earth metal propionates, over a period of 1 h at a temperature of 100° C. and a pressure in the range from 1 bar to 50 mbar, in particular 50 mbar.

In the method (A1) according to the invention) $M^{n+}$ is preferably an alkali metal, particularly preferably sodium or potassium, and very particularly preferably sodium. In the method (A1) according to the invention, the molar ratio of the neutral alkali metal propionate to propionic acid in the homogeneous mixture is preferably in the range from 1:0.4 to 1:3, and particularly preferably in the range from 1:0.5 to 1:2.5; e.g. about 1:1 or 1:2.

In the method (A1) according to the invention, in particular compounds of the formula (I) are obtained in which x is in the range from 0.4 to 3, and especially in the range from 0.5 to 2.5; e.g. about 1 or 2.

In a particularly preferred embodiment of the method (A1) according to the invention, $M^{n+}$ is sodium and the molar ratio of the neutral sodium propionate to propionic acid in the homogeneous mixture is in the range from 1:0.4 to 1:3, and particularly preferably in the range from 1:0.5 to 1:2.5; e.g. about 1:1 or 1:2. The acid sodium propionates obtained in this embodiment exhibit, in differential scanning calorimetry (DSC), a phase transition point, depending on their composition, in particular at a temperature of 61° C., and if appropriate at 90° C. In addition, the powder X-ray diffractogram of these acid sodium propionates is characterized, in particular, by diffraction peaks at least 4, in particular at least 5, and especially at least 7, lattice spacings selected from d=13.63; 13.13; 13.03; 11.09; 9.71; 9.59; 3.94; 2.84; 2.79 [Å] (±0.04 [Å]). Further diffraction peaks are frequently observed at the following lattice spacings: d=4.88; 4.14; 3.68; 3.46; 3.26;

3.09 and/or 2.96 [Å] (±0.04 [Å]). It is obvious to those skilled in the art that very close lattice spacings can be superimposed by one another in the powder X-ray diffractogram. This can occur, in particular, at the reflection positions for d=13.13 and 13.03 [Å] and d=9.71 and 9.59 [Å], so that in each case only one reflection is observed at this lattice spacing. Typical relative intensities obtained in this embodiment for x=2 (see example 1 hereinafter) and x=1 (see example 3 hereinafter) in the powder X-ray diffractogram are listed in table 1,

TABLE 1

| Diffraction peaks | d (±0.04) [Å] | $I_{rel}$ [%] (x = 2) | $I_{rel}$ [%] (x = 1) |
|---|---|---|---|
| 1 | 13.63 | 3.7 | 41.6 |
| 2 | 13.13 | 3.8 | — |
| 3 | 13.03 | — | 42.5 |
| 4 | 11.09 | 38.7 | 12.8 |
| 5 | 9.71 | — | 100 |
| 6 | 9.59 | 100 | — |
| 7 | 3.94 | 2.7 | 7.6 |
| 8 | 2.84 | 1.5 | 4.7 |
| 9 | 2.79 | 3.7 | 2.6 |

In the method (A2) according to the invention, $M^{n+}$ is preferably an alkaline earth metal, particularly preferably calcium or magnesium, and very particularly preferably calcium.

In the method (A2) according to the invention, the molar ratio of the neutral alkaline earth metal propionate to propionic acid in the homogeneous mixture is preferably in the range from 1:0.5 to 1:10, particularly preferably in the range from 1:1 to 1:8, and very particularly preferably in the range from 1:2 to 1:5, e.g. about 1:3.

In the method (A2) according to the invention, in particular compounds of the formula (I) are obtained in which x is in the range from 0.25 to 0.6, and especially in the range from 0.3 to 0.5, e.g. about 0.4.

In a particularly preferred embodiment of the method (A2) according to the invention, $M^{n+}$ is calcium and the molar ratio of the neutral calcium propionate to propionic acid in the homogeneous mixture is in the range from 1:1 to 1:8, and particularly preferably in the range from 1:2 to 1:5, erg. about 1:3. The acid calcium propionates obtained in this embodiment exhibit a phase transition point in differential scanning calorimetry in particular at a temperature in the range from 167 to 168° C. In addition, the powder X-ray diffractogram of these acid calcium propionates is characterized, in particular, by diffraction peaks at least 5, in particular at least 7, especially at least 9, and very especially all lattice spacings selected from d=12.70; 9.42; 8.91; 8.16; 6.65; 6.38; 4.51; 4.26; 4.03; 3.81 [Å] (±0.04 [Å]). Further diffraction peaks are frequently observed in this case at the following lattice spacings: d=24.86; 3.93; 3.32; 2.83 and/or 2.56 [Å] (±0.04 [Å]). Typical relative intensities obtained in this embodiment for x=0.4 (see example 4 hereinafter) in the powder X-ray diffractogram are listed in table 2.

TABLE 2

| Diffraction peaks | d (±0.04) [Å] | $I_{rel}$ [%] |
|---|---|---|
| 1 | 12.70 | 100 |
| 2 | 9.42 | 0.5 |
| 3 | 8.91 | 0.5 |
| 4 | 8.16 | 2.9 |
| 5 | 6.65 | 0.6 |
| 6 | 6.38 | 1.5 |
| 7 | 4.51 | 0.5 |
| 8 | 4.26 | 1.8 |

TABLE 2-continued

| Diffraction peaks | d (±0.04) [Å] | $I_{rel}$ [%] |
|---|---|---|
| 9 | 4.03 | 0.4 |
| 10 | 3.81 | 0.7 |

The method (A) according to the invention can be carried out continuously, semicontinuously or batchwise. It is particularly advantageous in the variant (A1) that a dry product is obtainable without using a drying step, and that the stoichiometry of the resultant compound of the formula (I) can be set freely over a wide range via selection of the molar ratio of the starting materials in the homogeneous mixture produced. Generally, compositions comprising compounds of the formula (I) can be produced in this manner which have a content of propionic acid in the range from 5 to 70% by weight, and in particular in the range from 10 to 65% by weight, based on the total weight of the composition.

The present invention further relates to a method (B) for producing a propionic acid-comprising composition in solid and essentially pure form, comprising at least one compound according to formula (I)

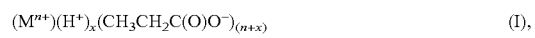

where
$M^{n+}$ is an n-valent alkali metal cation or alkaline earth metal cation, e.g. lithium, sodium, potassium, rubidium, cesium, beryllium, magnesium, calcium, strontium or barium; preferably sodium, potassium, magnesium or calcium; and particularly preferably sodium or calcium; n being equal to 1 or 2; and x is a number in the range from 0.25 to 5; preferably in the range from 0.3 to 3.5; and particularly preferably in the range from 0.3 to 2.5;

in which a homogeneous mixture is produced from the neutral alkali metal propionate or alkaline earth metal propionate and propionic acid in a molar ratio in the range of 1:0.25 to 1:5, with heating, and the homogeneous mixture is brought to crystallization, the water content of the homogeneous mixture, at least at the start of crystallization, and in particular also during it, being in the range from 1 to 15% by weight, based on the total weight of the mixture; and the molar ratio of the neutral alkali metal propionate or alkaline earth metal propionate to propionic acid in the homogeneous mixture not being in the range from 1:0.75 to 1:1.75, when $M^{n+}$ is potassium.

With respect to the neutral alkali (alkaline earth) metal propionates usable in this variant (B), the statements made above on the method (A) according to the invention apply.

In the variant (B), for producing the homogeneous mixture, use can be made not only of concentrated propionic acid, as in variant (A), but also an aqueous solution thereof. In the latter case, the aqueous propionic acid solution used preferably has a concentration of at least 95% by weight, more preferably at least 98% by weight. Particularly preferably, use is made of concentrated propionic acid having a propionic acid content of at least 99% by weight. The concentration of propionic acid or propionic acid solution is preferably in the range of 95 to 99% by weight.

If the neutral alkali (alkaline earth) metal propionates to be used are produced by reaction with propionic acid in aqueous solution, as explained above for method (A), in this case the molar ratios of the starting materials can advantageously be selected directly such that the components propionic acid, neutral alkali (alkaline earth) metal propionate and water in the resulting reaction batch are already in the abovementioned required molar ratios. In the variant (B), the mother liquor from the crystallization can also be used in the production of the homogeneous mixture.

The homogeneous mixture can be produced by combining the starting materials and heating the reaction mixture in the same manner as described above for variant (A). It is essential to the invention, here, in particular that crystallization proceeds from an aqueous solution. This can, as set forth above for (A2), have been or be admixed with seed crystals even before the start of crystallization. The aqueous solution is, preferably with continued stirring, brought to crystallization, e.g. by partial evaporation or by cooling, preferably by cooling. If the crystallization is caused or induced or accelerated by controlled evaporation of the liquid phase, preferably under vacuum, it is necessary to ensure that the molar ratios of the components in the solution lie within the ranges specified above at the start of crystallization.

After the crystallization the solid product, as described above for (A2), is separated from the mother liquor and preferably subjected to a drying step, likewise as described above for (A2). This produces compositions comprising compounds of the formula (I) which have dry contents as described above for (A1) or (A2). Compositions comprising compounds of the formula (I) may be produced which have a propionic acid content in the range from 5 to 70% by weight, and in particular in the range from 10 to 65% by weight, based on the total weight of the composition.

In a preferred embodiment of the method (B) according to the invention, $M^{n+}$ is an alkali metal, particularly preferably sodium or potassium, and very particularly preferably sodium.

In the method (B) according to the invention, the molar ratio of the neutral alkali metal propionate to propionic acid in the homogeneous mixture is preferably in the range from 1:8 to 1:2.2, and particularly preferably in the range from 1:1.9 to 1:2.1; e.g. about 1:2.

In this variant (B), in particular compounds of the formula (I) are obtained in which x is in the range from 1.8 to 2.2, and especially in the range from 2.1 to 2.2; e.g. about 2.

In a particularly preferred embodiment of the method (B) according to the invention, $M^{n+}$ is sodium and the molar ratio of the neutral sodium propionate to propionic acid in the homogeneous mixture is in the range from 1:1.8 to 1:2.2, and particularly preferably in the range from 1:1.9 to 1:2.1; e.g. about 1:2. The acid sodium propionates obtained in this embodiment exhibit, in differential scanning calorimetry (DSC), a phase transition point in particular at a temperature of 61° C., In addition, the powder X-ray diffractogram of these acid sodium propionates is characterized in particular by diffraction peaks at least 4, in particular at least 5, and especially at least 7, lattice spacings selected from d=13.63; 13.13; 13.03; 11.09; 9.71; 9.59; 3.94; 2.84; 2.79 [Å] (±0.04 [Å]). Further diffraction peaks are frequently observed in this case at the following lattice spacings: d=4.88; 4.14; 3.68; 3.46; 3.26; 3.09 and/or 2.96 [Å] (±0.04 [Å]). Typical relative intensities obtained in this case for x=2 (see example 5 hereinafter) in the powder X-ray diffractogram are listed in table 3.

TABLE 3

| Diffraction peaks | d (±0.04) [Å] | $I_{rel}$ [%] |
| --- | --- | --- |
| 1 | 13.63 | 3.7 |
| 2 | 13.13 | 3.8 |
| 3 | 11.12 | 38.7 |

TABLE 3-continued

| Diffraction peaks | d (±0.04) [Å] | $I_{rel}$ [%] |
| --- | --- | --- |
| 4 | 9.59 | 100 |
| 5 | 3.95 | 2.7 |
| 6 | 2.84 | 1.5 |
| 7 | 2.79 | 3.7 |

In a further preferred embodiment of the method (B) according to the invention, $M^{n+}$ is an alkaline earth metal, particularly preferably calcium or magnesium, and very particularly preferably calcium.

In the method (B) according to the invention, the molar ratio of the neutral alkaline earth metal propionate to propionic acid in the homogeneous mixture is preferably in the range from 1:0.5 to 1:10, particularly preferably in the range from 1:1 to 1:8, and very particularly preferably in the range from 1:2 to 1:5, e.g. about 1:3.

In this variant (B), in particular compounds of the formula (I) are obtained in which x is in the range from 0.25 to 0.6, and especially in the range from 0.3 to 0.5; e.g. about 0.4.

In a particularly preferred embodiment of the method (B) according to the invention, $M^{n+}$ is calcium and the molar ratio of the neutral calcium propionate to propionic acid in the homogeneous mixture is in the range from 1:1 to 1:8, and particularly preferably in the range from 1:2 to 1:5, e.g. about 1:3. The acid calcium propionates obtained in this embodiment have, in differential scanning calorimetry, a phase transition point in particular at a temperature in the range from 167 to 168° C. In addition, the powder X-ray diffractogram of these acid calcium propionates is characterized in particular by diffraction peaks at least 5, in particular at least 7, especially at least 9, and very especially, all lattice spacings selected from d=12.70; 9.42; 8.91, 8.16; 6.65; 6.38; 4.51; 4.26; 4.03; 3.81 [Å] (±0.04 [Å]). Further diffraction peaks are frequently observed in this case at the following lattice spacings: d=24.86; 3.93; 3.32; 2.83 and/or 2.56 [Å] (±0.04 [Å]). Typical relative intensities obtained in this case for x=0.4 (see example 6 and example 7 hereinafter) in the powder X-ray diffractogram correspond to the relative intensities listed in table 2 above for the respective reflection positions.

The method according to the invention (B) can be carried out continuously, semicontinuously or batchwise. Generally, compounds of the formula (I) can be produced in this manner which have a propionic acid content in the range from 5 to 70% by weight, and in particular in the range from 10 to 65% by weight, based on the total weight of the compound (I).

By means of the methods and method variants according to the invention, the compositions comprising the compounds of the formula (I) are obtained in solid and substantially pure form. These compositions comprising compounds of the formula (I) are novel and are therefore a further subject matter of the invention. According to the invention the compositions comprise at least one, e.g. 1, 2 or more, compounds of the formula (I). Preferably, the compositions essentially comprise a compound of the formula (I), in particular in pure form, or a mixture of two compounds of the formula (I).

The compounds of the formula (I) are distinguished, in particular, by a lower vapor pressure, compared with free propionic acid, and therefore by an increased stability and good handlability. The compositions according to the invention comprising compounds of the formula (I) can have a propionic acid content in the range from 5 to 70% by weight, and in particular in the range from 10 to 65% by weight, based on the total weight of the composition. The propionic acid content in the dry product can be determined in a customary manner, e.g. by titration of the propionic acid with a base.

The compounds of the formula (I) or the compositions comprising these are typically obtained in crystalline form. They correspond essentially or completely to the formula (I): $(M^{n+})(H^+)_x(CH_3CH_2C(O)O^-)_{(n+x)}$, x and n having the meanings given above. It is essential to the invention in this context that the compositions have alkali (alkaline earth) metal propionate and propionic acid in associated crystalline form. The inventively obtained crystalline modifications of the compounds of the formula (I) may be identified, for example, via X-ray wide-angle scattering. Unwanted modifications, e.g. free neutral metal propionates, can be qualitatively detected likewise by the same method. The X-ray diffraction peaks are stated in the present application in the form of the lattice spacings d [Å] independent of the wavelength of the x-rays used, which can be calculated from the measured diffraction angle by means of the Bragg equation.

Generally, the powder X-ray diffractogram of the compositions according to the invention has all of the diffraction peaks characteristic of the special crystal structure as stated above, e.g. for the acid sodium propionates or calcium propionates produced by the method according to the invention. Depending on the degree of crystallinity and the texturizing of the resultant crystals, however, weakening of the intensity of the diffraction peaks in the powder X-ray diffractogram can occur, which can go so far that individual low-intensity diffraction peaks are no longer detectable in the powder X-ray diffractogram. Individual low-intensity diffraction peaks can therefore be absent, or the intensity ratio in the powder X-ray diffractogram can be changed. The presence of all of the respectively stated diffraction peaks in the powder X-ray diffractogram is an indication that these are compositions having one or more compound(s) (I) of particularly high crystallinity. It is obvious for those skilled in the art that the inventive compositions or compounds (I), in addition to the respectively stated characteristic diffraction peaks, can have further diffraction peaks. In addition, mixtures of the inventive compositions comprising the compounds (I) with other crystalline compounds generally have additional diffraction peaks.

By means of differential scanning calorimetry (DSC), in the case of the inventive compositions, customarily one or more phase transition point(s) may be observed. It is assumed that each observed phase transition point is to be assigned to another compound of the formula (I), so that the occurrence of two peaks in the DSC indicates the presence of two compounds of the formula (I) in the inventive compositions. However, this interpretation is not to be considered limiting, since, e.g., an individual compound of the formula (I) having two phase transition points could also be present.

The fraction of compounds of the formula (I) in the if appropriate dry compositions obtained by the method according to the inventions is customarily at least 97% by weight, in particular at least 98% by weight, and especially at least 99% by weight, in each case based on the total weight of the dry composition. In this context, the expression "essentially in pure form" is also to be taken to mean, for the purposes of the present invention, that the inventive compositions comprising one or more compounds of the formula (I) can comprise, as further components, e.g. owing to residual moisture or crystallized residual moisture, generally up to 1.5% by weight of propionic acid, up to 1.5% by weight of neutral alkali (alkaline earth) metal propionate and/or up to 1% by weight of water, in each case based on the total weight of the composition. In particular, the water content in the inventive compositions, if appropriate after a drying step has been carried out, is at most 0.5% by weight, based on the total weight of the composition. Especially in the production variant (A1), the values are frequently markedly below said limit values.

Moreover, the inventively obtained compounds of the formula (I) are sufficiently stable to ensure easy handling and (further) processing. Moreover, the potassium ion content of the compositions obtained, provided that $M^{n+}$ is not potassium, is generally at most 1000 ppm, and in particular at most 500 ppm, in each case based on the total weight. The chloride content due to production conditions in the inventively obtained compositions is generally less than 1500 ppm, and in particular less than 1000 ppm, in each case based on the total weight.

Aqueous solutions of the inventive compositions comprising compounds of the formula (I) generally have pHs which differ markedly from the pHs of solutions of propionic acid of the same concentration or of the corresponding neutral propionates. For instance, e.g. a 10% strength by weight solution of sodium dipropionate at 20° C. has a pH of 4.9, and a 10% strength by weight solution of sodium tripropionate has a pH of 4.6; whereas a 10% strength by weight solution of neutral sodium propionate at 20° C. has a pH of 7 to 8. A 10% strength by weight solution of dicalcium pentapropionate has, at 20° C., a pH in the range from 5 to 6, whereas a 10% strength by weight solution of neutral calcium propionate has, at 20° C., a pH in the range from 8 to 10. A 10% strength by weight solution of propionic acid, in contrast, has at 20° C. a pH of 2.5.

The resultant solid product can, before and/or after a drying step, be comminuted, e.g. by means of mortars, cutting apparatuses, punching presses and cylinder mills, agglomerated, e.g. by means of mixers, and/or compacted, e.g. by means of presses and compacters. The apparatuses used for such a comminution are known to those skilled in the art.

Depending on the desired application, the composition produced according to the invention and comprising one or more compounds of the formula (I) can be further processed, in particular powders of defined particle sizes can be generated, the particles generated can be covered with coatings and/or mixtures with other additives can be produced. As examples of coatings or coating materials, mention may be made of oils such as soybean oil, fats and fatty acids such as palmitic or stearic acid, or polymer coatings, e.g. made of polyalkylenes and derivatives thereof. Customary additives are, in particular, flow aids such as silicic acid etc. Customary methods for coating and also the additives coming into consideration therefor are known in principle to those skilled in the art for the respective field, see, e.g., DE 102 31 891 A1.

According to the invention, the composition produced is in solid form, in particular as crystallizate powder, or as granules or compactate. Depending on use requirements, the powders, granules or compactates have a mean particle size in the range from 1 μm to 10 000 μm, in particular from 10 μm to 1000 μm, and especially from 100 μm to 500 μm.

The solid composition produced according to the invention and comprising at least one compound of the formula (I), or formulations comprising these, are suitable, in particular, for use as silage agents or silage additives in the production of silage. The reduction in pH caused by them, e.g. to the order of magnitude of about 3 to 4, counteracts an occurrence of putrefactive bacteria, in particular, the development of harmful yeasts is inhibited. The lactic acid fermentation can be accelerated, or secondary fermentation can be prevented.

The solid composition produced according to the invention and comprising at least one compound of the formula (I) is also suitable as what is termed as acidifier. Acidifiers are taken to mean those substances which lower the pH. The expression comprises not only those substances which lower the pH in the substrate (e.g. animal feed), but also those which lower the pH in the gastrointestinal tract of an animal.

The solid composition produced according to the invention and comprising at least one compound of the formula (I) is suitable, in addition, as preservative, in particular as preservative for green fodder and/or animal feed.

The solid composition produced according to the invention and comprising at least one compound of the formula (I) is suitable, in addition, as food supplement.

The solid composition produced according to the invention and comprising at least one compound of the formula (I) or formulations comprising these are also suitable for use in feedstuffs for animals (animal feedstuffs), in particular as additive to animal feed in the form of feedstuff additives and especially as additive to premixes for animal feedstuffs. Premixes are mixtures which generally comprise minerals, vitamins, amino acid, trace elements and if appropriate enzymes. Animal feedstuff and feedstuff additives which comprise the solid composition produced according to the invention and comprising compounds of the formula (I) are particularly suitable for monogastric animals such as hogs, especially piglets, breeding sows and porkers, and also poultry, especially broilers, laying hens, turkeys, ducks, geese, quails, pheasants and ostriches.

Depending on the other substances or additives present in the feedstuff or feedstuff additive, the content of the solid composition produced according to the invention and comprising compounds of the formula (I) in the feedstuff or feedstuff additive can vary greatly. In feedstuff additives, the content also depends on the type of the formulation, e.g. on the addition of aids such as desiccants, on a possible coating and on the residual moisture content. Customarily, the content of solid composition produced according to the invention and comprising compounds of the formula (I) in the feedstuff additive is, e.g., in the range from 0.1 to 99.5% by weight, in particular from 0.5 to 75% by weight, and especially from 1 to 50% by weight, based on the total dry weight of the feedstuff additive. The solid composition produced according to the invention and is also suitable for use in a premix and can in this case be used, e.g. added, in the customary amounts.

In particular, in the case of use in animal feedstuff and feedstuff additives for poultry, a low content of potassium ions is advantageous, since potassium in this case can exhibit a diuretic action. The use of compositions produced according to the invention in which $M^{n+}$ is, e.g. sodium, for the abovementioned purpose thus represents an acid sodium and propionate source without the fraction of potassium ions being necessarily increased. For instance, a solid feedstuff additive can be formulated which comprises the solid composition or compound (I) produced according to the invention and is essentially free from potassium ions. In this case, essentially free from potassium ions means that the potassium ion content is at most 1000 ppm, and in particular at most 500 ppm, in each case based on the weight of the feedstuff additive.

Animal feedstuffs are composed in such a manner that the corresponding nutrient requirement for the respective animal species is optimally covered. Generally, plant feedstuff components such as maize, wheat or barley meal, whole soybean meal, soybean extraction meal, linseed extraction meal, rapeseed extraction meal, green flour or pea meal are selected as crude protein sources. To ensure corresponding energy content of the feedstuff, soybean oil or other animal or vegetable fats are added. Since the plant protein sources comprise some essential amino acids only in insufficient quantity, feedstuffs are frequently enriched with amino acids. These are primarily lysine and methionine. To ensure the mineral and vitamin supply of the farm animals, in addition minerals and vitamins are added. The type and amount of added minerals and vitamins depends on the animal species and is known to those skilled in the art (see, e.g., Jeroch et al., Ernährung landwirtschaftlicher Nutztiere [Nutrition of farm animals], Ulmer, U T B). To cover the nutrient and energy requirement, complete feeds can be used which comprise all nutrients in a ratio to one another covering requirements. It can form the sole feed of the animals. Alternatively, a supplementary feed can be added to a grain feed made of cereals. This relates to protein-, mineral- and vitamin-rich feed mixtures which supplement the feed.

For many of the abovementioned purposes, in particular in the field of animal nutrition, foods and preservatives and silage, it can be advantageous to combine the inventive compositions comprising at least one compound of the formula (I) with further solids known for said purposes in one formulation. A suitable substance for this is, in particular, the acid sodium diformate in solid form described in the previous German application DE 10 2005 017 089.7 of the applicant.

The examples hereinafter serve to illustrate the invention and are in no way to be taken as limiting.

EXAMPLES

Production Method A

Variant A1

Example 1

Sodium tripropionate [$NaH_2(CH_3CH_2C(O)O)_3$]

555 g of propionic acid and 350 g of sodium propionate were added to a 0.5 l stirred vessel equipped with jacket bottom outlet valve, anchor agitator and cryostat and heated to 70° C. until a homogeneous melt was obtained. The melt was drained off into a metal shell and set on cooling. The resultant solid (858 g) which was comminuted and dried for 6 h at 45° C. under a water-jet vacuum had a propionic acid content of 61.64% by weight and a water content of 0.08% by weight.

Example 2

Acid sodium propionate [$NaH(CH_3CH_2C(O)O)_{2.3}$]

The procedure of example 1 was followed, 400 g of propionic acid and 400 g of sodium propionate being used. The resultant comminuted solid (762 g) had a propionic acid content of 49.77% by weight and a water content of 0.03% by weight.

Example 3

Sodium dipropionate [$NaH(CH_3CH_2C(O)O)_2$]

The procedure of example 1 was followed, 390 g of propionic acid and 500 g of sodium propionate being used and the mixture being heated to 165° C. until a homogeneous liquid mixture was obtained. The resultant comminuted solid (817 g) had a propionic acid content of 43.46% by weight and a water content of 0.19% by weight.

Variant A2

Example 4

Acid calcium propionate [CaH$_{0.4}$(CH$_3$CH$_2$C(O)O)$_{2.4}$]

680 g of propionic acid and 590 g of calcium propionate were added to a 1 l stirred vessel equipped with jacket, bottom outlet valve, anchor agitator and cryostat and heated to 134° C. until a solution was obtained. The solution was cooled slowly to 22° C., in which case crystallization started. After cooling, the solid crystallized out was obtained by centrifugation (470 g, of which 0.93% by weight water). The resultant solid which was dried overnight at 50° C. under a water-jet vacuum had a propionic acid content of 13.86% by weight and a water content of 0.42% by weight.

Production Method B

Example 5

Sodium tripropionate [NaH$_2$(CH$_3$CH$_2$C(O)O)$_3$]

800 g of propionic acid, 450 g of sodium propionate and 100 g of water were added to a 1 l stirred vessel equipped with jacket, bottom outlet valve, anchor agitator and cryostat and heated to 50° C. until a solution was obtained. The solution was cooled to 31° C. and then seeded with 1 g of sodium tripropionate crystals. The reaction mixture was cooled to 22° C. After cooling, the solid crystallized out was obtained by centrifugation (349 g, of which 2.18% by weight water). The resultant solid which was dried overnight at 40° C. under a water-jet vacuum had a propionic acid content of 61.29% by weight and a water content of 0.06% by weight.

Example 6

Acid calcium propionate [CaH$_{0.4}$(CH$_3$CH$_2$C(O)O)$_{2.4}$]

750 g of propionic acid, 575.8 g of calcium propionate and 38.6 g of water were added to a 1 l stirred vessel equipped with jacket, bottom outlet valve, anchor agitator and cryostat and heated to 125° C. until a solution was obtained. The solution was cooled to 112° C. and then seeded with crystals of acid calcium propionate. The reaction mixture was cooled to room temperature, in which case crystallization started at 109° C. After cooling, the solid crystallized out was obtained by centrifugation. The resultant solid (302.6 g) which was dried at 75° C. under a water-jet vacuum had a propionic acid content of 13.73% by weight and a water content of 0.05% by weight.

Example 7

Acid calcium propionate [CaH$_{0.4}$(CH$_3$CH$_2$C(O)O)$_{2.4}$]

621.2 g of propionic acid, 543 g of calcium propionate and 155.3 g of water were added to a 1 l stirred vessel equipped with jacket, bottom outlet valve, anchor agitator and cryostat and heated to 77° C. until a solution was obtained. The solution was cooled to 70° C. and then seeded with crystals of acid calcium propionate. The reaction mixture was cooled to room temperature, in which case crystallization started at 65° C. After cooling, the solid crystallized out was obtained by centrifugation (129.9 g, of which 1.61% by weight water). The resultant solid dried at 75° C. under a water-jet vacuum had a propionic acid content of 13.89% by weight and a water content of 0.01% by weight.

X-ray Structure Analysis

The crystal structures of the compounds [CaH$_{0.4}$(CH$_3$CH$_2$C(O)O)$_{2.4}$] (structure I) and [NaH$_2$(CH$_3$CH$_2$C(O)O)$_3$] (structure II) obtained from the production examples were determined by direct methods using the SHELXTL program. The correct positions of the calcium and sodium atoms were derived from the E map. By subsequent "least-squares" refinement (i.e. Least Squares Method) and calculation of the differential electron density, the residual non-hydrogen atoms were assigned. The atoms were refined anisotropically and the hydrogen atoms set to idealized positions. Tables 4 and 5 hereinafter summarize the results thus obtained.

[CaH$_{0.4}$(CH$_3$CH$_2$C(O)O)$_{2.4}$]  (structure I)

TABLE 4

| Structure I | monoclinic |
|---|---|
| Spatial group | P2$_1$/n |
| a | 15.8 |
| b | 13.6 |
| c | 16.8 |
| α | 90 |
| β | 114.31 |
| γ | 90 |
| Volume | 2802.2451 |
| Z | 4 |
| Density (calculated) | |
| R1, wR2 | 0.091; 0.242 | a, b, c = length of the edges of the unit cell
α, β, γ = angles of the unit cell
Z = number of molecules in the unit cell
R1 = Σ||F$_o$| − |F$_c$||/Σ|F$_o$|
wR2 = {Σ[w(F$_o^2$ − F$_c^2$)$^2$]/Σ[w(F$_o^2$)$^2$]}$^{1/2}$ The asymmetric unit of the crystal of the structure I is shown in FIG. 1 and comprises four Ca propionate fractions and an uncharged propionic acid fraction. A calcium ion sits on a special position and counts only ½. Coordination of the calcium ions is not very symmetrical. The hydrogen of the OH group forms a hydrogen bond to the adjacent propionate. If a plurality of unit cells are viewed together, it is possible to see how the crystal is composed from two layers. The methyl groups develop hydrophobic surfaces at the top and bottom. In between there is a layer having ionic interactions. In one orientation, tube-like structures form having a polar core and hydrophobic surface.

[NaH$_2$(CH$_3$CH$_2$C(O)O)$_3$]  (structure II)

TABLE 5

| Structure II | triclinic |
|---|---|
| Spatial group | P-1 |
| a | 6.8962 |
| b | 11.1333 |
| c | 17.0488 |
| α | 95.064 |
| β | 91.585 |
| γ | 100.971 |
| Volume | 1278.7 |
| Z | 2 |
| Density (calculated) | |
| R1, wR2 | 0.2173; 0.5245 | a, b, c = length of the edges of the unit cell
α, β, γ = angles of the unit cell
Z = number of molecules in the unit cell
R1 = Σ||F$_o$| − |F$_c$||/Σ|F$_o$|
wR2 = {Σ[w(F$_o^2$ − F$_c^2$)$^2$]/Σ[w(F$_o^2$)$^2$]}$^{1/2}$ The asymmetric unit of the crystal of the structure II is shown in FIG. 2 and comprises 2 Na propionate fractions and 4 propionic acid fractions. Although the R factor is very poor at 0.22, the correctness of the structure is assumed without any binding restriction of the invention being seen herein. The crystals form platelets which lie slightly twisted one above the other, which can explain impaired resolution. When a plurality of unit cells are considered, it is noted that the tubular structure is here still more pronounced than in the case of structure I.

The invention claimed is:

1. A propionic acid-comprising composition in solid and essentially pure form, comprising at least one compound according to formula (I)

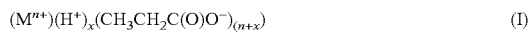  (I)

wherein
$M^{n+}$ is sodium;
n is 1; and
x is a number in the range from 1.8 to 2.2;
or [NaH$_2$(CH$_3$CH$_2$C(O)O)$_3$];
or [NaH$_{1.3}$(CH$_3$CH$_2$C(O)O$_{2.3}$)];
and wherein said composition exhibits powder X-ray diffractogram diffraction peaks at 4 or more of the following lattice spacings d: 13.63; 13.13; 13.03; 11.09; 9.71; 9.59; 3.94; 2.84; 2.79 [Å] (±0.04 [Å]).

2. The composition of claim 1, wherein said compound of formula (I) is present in crystalline form.

3. The composition of claim 1, wherein said composition has a water content of 1% or less by weight based on the total weight of the composition.

4. The composition of claim 1, wherein said composition exhibits a phase transition point at a temperature of 61° C., as determined by means of differential scanning calorimetry.

5. A silage additive, preservative, acidifier, food supplement, feedstuff, or feedstuff additive for animal feed comprising a composition of claim 1.

* * * * *